(12) United States Patent
Danieli et al.

(10) Patent No.: US 7,381,823 B2
(45) Date of Patent: Jun. 3, 2008

(54) PROCESS FOR PREPARING CYCLOHEXANEDIACETIC ACID MONOAMIDE

(75) Inventors: Bruno Danieli, Milan (IT); Pietro Delogu, Trieste (IT); Sabrina De Rosa, Cervignano del Friuli (IT); Lorenza Fugazza, San Fiorano (IT)

(73) Assignee: Serichim S.R.L., Torviscosa (IT)

( * ) Notice: Subject to any disclaimer, the term of this patent is extended or adjusted under 35 U.S.C. 154(b) by 93 days.

(21) Appl. No.: 10/599,009

(22) PCT Filed: Mar. 17, 2005

(86) PCT No.: PCT/EP2005/051243

§ 371 (c)(1),
(2), (4) Date: Sep. 18, 2006

(87) PCT Pub. No.: WO2005/090310

PCT Pub. Date: Sep. 29, 2005

(65) Prior Publication Data

US 2007/0208175 A1     Sep. 6, 2007

(30) Foreign Application Priority Data

Mar. 17, 2004   (IT)   .................. MI2004A0501

(51) Int. Cl.
*C07D 221/20*   (2006.01)
*C07C 53/134*   (2006.01)
(52) U.S. Cl. .................. 546/16; 562/512; 562/507
(58) Field of Classification Search .................. 546/16; 562/512, 507

See application file for complete search history.

(56) References Cited

U.S. PATENT DOCUMENTS 6,613,904 B2   9/2003   Montanari

OTHER PUBLICATIONS

Thole, F.B. et al.; "The Formation And Reaction Of Imino-Compounds. Part Xv. The Production Of Imino-Derivatives Of Piperidine Leading To The Formation Of The Bβ-Disubstituted Glutaric Acids"; Journal of the Chemical Society, Transactions, Chemical Society, Letchworth, GB, No. 99, 1911, pp. 422-448.
Atkinson et al.; "Mechanism Of The Boron Trifluoride-Catalysed Cyclisation Of Some Cyclo-Octenylidene Derivatives"; J.Chem. Soc., Perkin Trans 1, No. 23, 1976, pp. 2457-2462.
Al-Rawi et al., Heterocyclic Synthesis with Malonyl Chloride. Part XI. Reactions of 2-Alkyl-or(-Aryl-)thio-7-chloropyrano[3,4-e][1,3]oxazine-4,5-diones with Water and with Alcohols; Helv. Chim.Acta, vol. 50, No. 4, pp. 22-34.
Kon et al.; "Chemistry Of The Three-Carbon System. Part VII Derivatives Of Malonic Acid"; J.Chem.Soc., Abstracts, 1926, pp. 2727-2735.
Database Registry (online); RN 780785-83-3, Nov. 15, 2004, retrieved from STN.

*Primary Examiner*—Charanjit S Aulakh
(74) *Attorney, Agent, or Firm*—Gifford, Krass, Sprinkle, Anderson & Citkowski, P.C.

(57) ABSTRACT

A new process is described for synthesising cyclohexanediacetic acid monoamide, a key compound in the synthesis of grabapentin precursors. The process of the invention is characterised by reacting cyclohexanone with cynoacetamide and immediately after, with a suitable malonic acid ester. A new intermediate (5-cyano-2,4-dioxo-3-azaspiro[5,5]undecane-1-carboxylic acid ester) is obtained which is convertible, under mild reaction conditions, into cyclohexanediacetic acid monoamide.

9 Claims, No Drawings

PROCESS FOR PREPARING CYCLOHEXANEDIACETIC ACID MONOAMIDE

FIELD OF THE INVENTION

The present invention concerns the synthesis of gabapentin precursors. A new process is described for synthesising cyclohexanediacetic acid monoamide.

PRIOR ART

Cyclohexanediacetic acid monoamide, or 3,3-pentamethylene mono glutaramide, hereinafter known as MAAC, is an important intermediate for preparing a medicinal known by the generic name of Gabapentin, [1-(aminomethyl)cyclohexyl]acetic acid. The preparation of MAAC is described for example in U.S. Pat. No. 4,024,175 and WO 03002517, by treating 3,3-pentamethyleneglutaric anhydride with aqueous ammonia. The pentamethyleneglutaric anhydride in turn is obtained from cyclohexanediacetic acid, which is prepared by acid hydrolysis of the cyclic imide known by the IUPAC name 1,5-dicarbonitrile-2,4-dioxo-3-azaspiro[5,5]undecane. This cyclic imide is in turn obtained from cyclohexanone with ethyl cyanoacetate. This long series of passages is described for example in patents U.S. Pat. Nos. 5,132,451, 6,521,788, 6,613,904, WO 03002504 and others. The synthesis sequence is summarised in scheme 1.

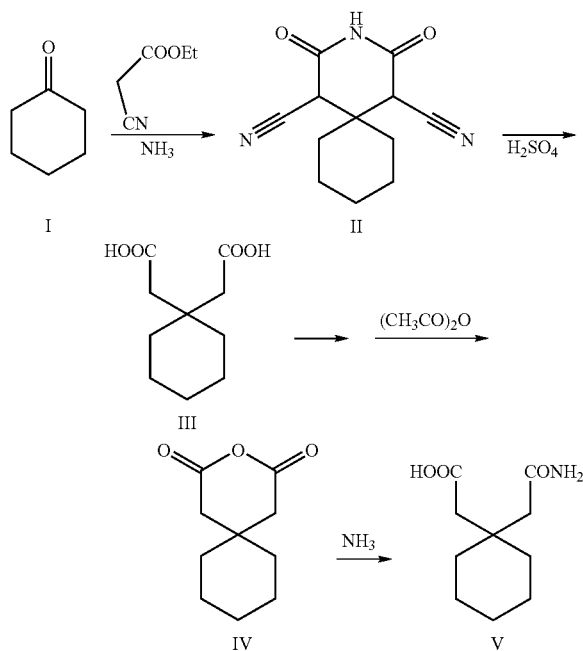

Some of the reactions in Scheme 1 are particularly difficult and onerous to apply industrially. For example the transformation of cyclohexanone into the cyclic imide II requires reaction times of about 72 hours (see for example GB 898692), while hydrolysis of the imide II into the diacid III occurs at high temperature in the presence of concentrated sulphuric acid, and involves the production of large quantities of waste products. There is therefore a strong need for a method for preparing MAAC which avoids the difficulties described, being both industrially convenient and ecologically compatible.

SUMMARY OF THE INVENTION

A new process is described for synthesising cyclohexanediacetic acid monoamide (3,3-pentamethylene mono glutaramide), a key compound in the synthesis of gabapentin precursors.

The process of the invention is characterised by reacting cyclohexanone with cyanoacetamide and thereafter, with a suitable malonic acid ester. A new intermediate (5-cyano-2,4-dioxo-3-azaspiro[5,5]undecane-1-carboxylic acid ester) is obtained which is convertable, under mild reaction conditions, into cyclohexanediacetic acid monoamide.

DETAILED DESCRIPTION OF THE INVENTION

This invention provides a simplified process for preparing MAAC. This process is based on the preparation of a new intermediate, not previously described, which can be easily transformed into the monoamide V. This intermediate has the formula VI:

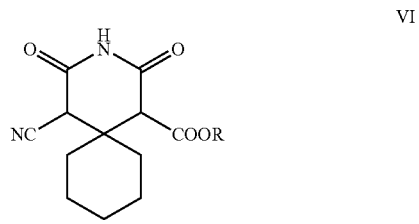

where R can be hydrogen, alkyl, substituted alkyl, benzyl; preferred examples of alkyls are C1-C10 and more preferably C1-C5 alkyls.

While being structurally similar to the imide II, the reactivity of the new imide VI is very different. It is known that transformation of the imide II into cyclohexanediacetic acid III requires the use of sulphuric acid at high temperature. Patent WO 03002504 hypothesises that during the reaction, a tricyclic compound may form which would be particularly stable.

The cyclohexaneacetic acid thus obtained is transformed into MAAC by means of the two successive reactions of anhydride formation and ammonolysis. A three step process is involved, the first of which requires particularly severe conditions. Instead, it has been established that the imide VI can be transformed into MAAC in only two reaction passages which both occur under particularly mild conditions. In conclusion, the imide VI can be prepared by much faster reactions than the imide II and can be transformed into MAAC by a more direct process under milder conditions.

The imide VI can be prepared starting from raw materials which are easily available and of low cost. The synthesis sequence is the following:

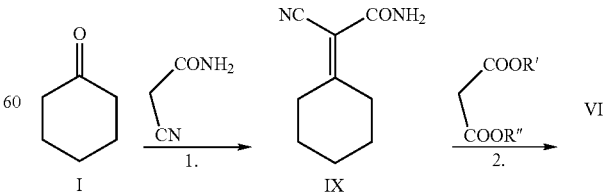

Reaction 1. consists of condensing the cyclohexanone (I) with cyanoacetamide, to obtain 2-cyclohexylidene-2-cyanoacetamide (IX); this reaction can be undertaken for example in toluene, in the presence of ammonium acetate and acetic acid, heating to a temperature between 20 and 150° C., and preferably to the reflux temperature of the reaction mixture; the compound IX is separated from the reaction mixture.

Reaction 2. consists of condensing 2-cyclohexylidene-2-cyanoacetamide with the malonic acid ester shown above, where R' and R'', the same or different, represent alkyl, substituted alkyl, benzyl. The reaction is carried out in the presence of a base, such as sodium hydride or sodium alcoholate; the compound VI, where R represents alkyl, substituted alkyl or benzyl, is obtained by then acidifying the reaction mixture; the compound VI where R is H can be easily obtained by subjecting the product VI where R is e.g. benzyl to catalytic hydrogenation, for example in the presence of Pd/C.

Reactions 1. and 2. can also be undertaken by operating in a single reactor and without isolating the compound IX; the reaction therefore takes place according to the following scheme:

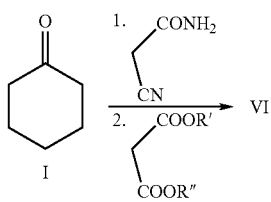

where R has the aforesaid meanings.

Transformation of the imide VI into MAAC (V) can be favourably obtained under mild conditions with classical organic chemistry methods, for example by hydrolysis and decarboxylation; the intermediate VII is thus obtained, which is further hydrolysed to obtain MAAC (V).

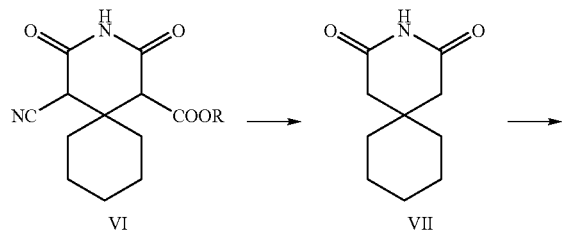

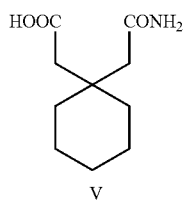

In the passage VI to VII, hydrolysis can be undertaken in a basic environment (achieved for example with an alkali or alkaline-earth metal hydroxide) and decarboxylation by subsequent acidification of the reaction mixture. Hydrolysis of the cyano group can be possibly favoured by the presence of hydrogen peroxide, or by reagents and operating conditions given in the literature (see for example S. March, Advanced Organic Chemistry, 4th Edition, New York, 1992, pages 887-888; R. C. Larock, Comprehensive Organic Transformations, 2nd Edition, New York, pages. 1986-1987).

Given the acidic nature of the hydrogen of the imide group, it is presumed that hydrolysis in a basic environment takes place on the anion of the amide VI having the following formula

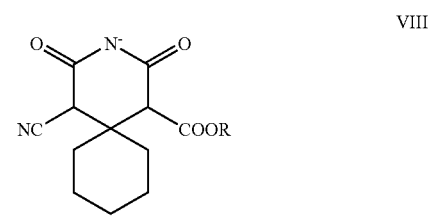

Decarboxylation can be undertaken in an acid environment, for example with an acid hydrohalogen or sulphuric acid.

Subsequent hydrolysis of VII to V can be undertaken for example by heating with alkali in an aqueous environment; after cooling, the product V precipitates by acidification.

The passages VI→VII→V can also be effected continuously in the same reactor, thus without the need to isolate the intermediate VII.

The products derived from hydrolysis of the imide VI, usable as intermediates for preparing gabapentin (X), are numerous and enable alternative pathways for synthesising the active principle to be chosen. Scheme 2 indicates the various possibilities:

Scheme 2

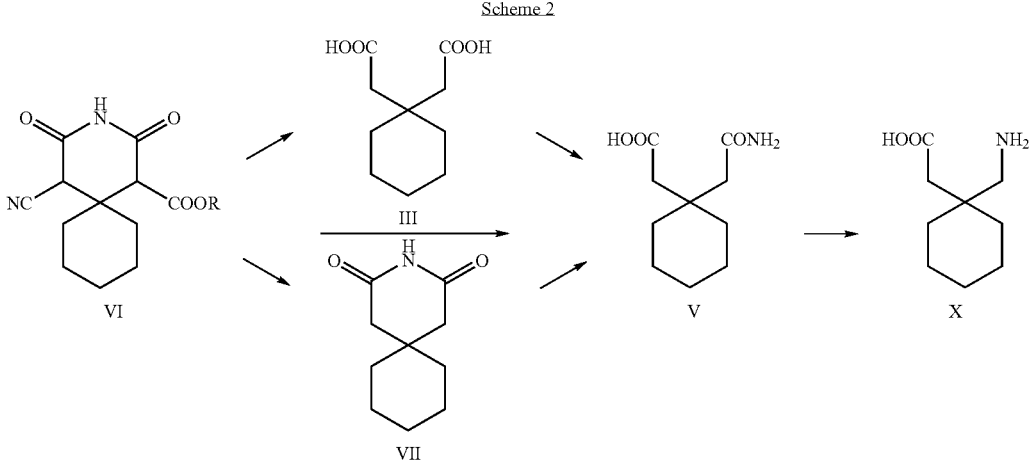

The aforedescribed invention is illustrated by the following non-limiting examples.

EXPERIMENTAL PART

Example 1

Synthesis of 2-cyclohexylidene-2-cyanoacetamide (IX)

600 ml of toluene, 200 g of cyanoacetamide, 193 g of cyclohexanone, 15 g of ammonium acetate and 24 g of acetic acid are placed in a 2 litre flask equipped with a mechanical stirrer, thermometer and Dean-Stark trap connected to a condenser, under nitrogen flow. The mixture is heated under reflux, simultaneously separating the water by distilling the water-toluene azeotrope. The separated water is collected in the Dean-Stark trap and removed at suitable time intervals. After 2 hours, on completion of the azeotropic distillation, it is cooled to 70° C., washed with 400 ml of a saturated sodium bicarbonate solution and cooled to 15° C. The precipitated solid is filtered off, washed with 70 ml of toluene, then 70 ml of water and dried in an oven at 40° C. under vacuum. 213 g of 2-cyclohexylidene-2-cyanoacetamide are obtained.

Example 2

Synthesis of ethyl 5-cyano-2,4-dioxo-3-azaspiro[5,5]undecane-1-carboxylate (VI)

0.69 g of sodium metal are suspended in 30 ml of anhydrous ethanol in a 100 ml flask equipped with a magnetic stirrer, thermometer and condenser, in a nitrogen atmosphere. When the sodium has dissolved, 4.8 g of diethylmalonate are added followed, after 15 minutes, by 4.92 g of cyclohexylidenecyanoacetamide. The mixture is left for 1 hour under agitation at 25° C. and then acidified with 36% HCl. The solid obtained is filtered off and dried under vacuum. 6.84 g of ethyl 5-cyano-2,4-dioxo-3-azaspiro[5,5]undecane-1-carboxylate are obtained.

Melting range: 167-170° C. $^1$H-NMR (acetone-d6, 200 MHz), δ(ppm): 4.60 (s, 1H), 4.28 (q, 2H), 4.09 (s, 1H), 1.8-1.5 (m, 10H), 1.39 (t, 3H). $^{13}$C-NMR (DMSO-d6, 75.4 MHz), δ(ppm): 167.97, 167.12, 165.29, 115.07, 62.21, 52.48, 40.69, 38.73, 35.11, 31.08, 24.58, 20.30, 20.17, 13.77.

Example 3

Synthesis of methyl 5-cyano-2,4-dioxo-3-azaspiro[5,5]undecane-1-carboxylate (VI)

24 ml of a 5.4 M solution of sodium methylate in methanol, 17.7 g of dimethylmalonate and 100 ml of methanol are placed in a 250 ml flask equipped with a mechanical stirrer, thermometer and condenser, under nitrogen flow. After 30 minutes, when the sodium has completely dissolved, a suspension of 20 g cyclohexylidenecyanoacetamide in 50 ml of methanol is added over a period of 15 minutes. The reaction mixture is left under agitation for 1 hour at 25° C. and is subsequently acidified with 5% HCl. The solid obtained is filtered off, washed with methanol and dried under vacuum. 28 g of methyl 5-cyano-2,4-dioxo-3-azaspiro[5,5]undecane-1-carboxylate are obtained.

HPLC-MS: [M-H]$^-$: 263 Melting range: 180.5-181.2° C.

Example 4

Synthesis of benzyl 5-cyano-2,4-dioxo-3-azaspiro[5,5]undecane-1-carboxylate (VI)

3.41 g of dibenzylmalonate, 30 ml of toluene and 0.58 g of 60% sodium hydride in mineral oil are placed in a 100 ml flask equipped with a magnetic stirrer, thermometer and condenser, in a nitrogen atmosphere. After 15 minutes, 1.97 g of cyclohexylidenecyanoacetamide are added. The reaction mixture is left under agitation for 6 hours at 25° C. and is then acidified with 36% HCl. The organic phase is separated and the solvent is evaporated under reduced pressure to obtain 3.18 g of benzyl 5-cyano-2,4-dioxo-3-azaspiro[5,5]undecane-1-carboxylate.

Melting range: 153-156° C. $^1$H-NMR (CDCl$_3$, 200 MHz), δ(ppm): 8.2 (bs, 1H), 7.5-7.4 (m, 5H), 5.34, 5.15 (AB system, J=14 Hz, 2H), 4.5 (s, 1H), 4.1 (s, 1H), 1.8-1.1 (m, 10H).

Example 5

Synthesis of 5-cyano-2,4-dioxo-3-azaspiro[5,5]undecane-1-carboxylic acid (VI)

1.8 g of benzyl 5-cyano-2,4-dioxo-3-azaspiro[5,5]undecane-1-carboxylate, 25 ml of ethyl acetate and 0.09 g of 5% Pd/C are placed in a 100 ml flask equipped with a magnetic stirrer, thermometer and condenser. The mixture is stirred for 4 hours at 12° C. under a hydrogen atmosphere. 10 ml methanol are added and the mixture is filtered through celite. The solvent is evaporated at 20° C. under reduced pressure to obtain 1.32 g of 5-cyano-2,4-dioxo-3-azaspiro[5,5]undecane-1-carboxylic acid.

Melting range: 210-214° C. $^1$H-NMR (DMSO-d6, 200 MHz), δ(ppm): 11.8 (s, 1H), 4.7 (s, 1H), 3.9 (s, 1H), 1.8-1.0 (m, 10H).

Example 6

Synthesis of 2,4-dioxo-3-azaspiro[5,5]undecane (VII)

10 g of methyl 5-cyano-2,4-dioxo-3-azaspiro[5,5]undecane-1-carboxylate and 5 g of NaOH dissolved in 125 ml of 2:1 ethanol/water are placed in a 250 ml flask equipped with mechanical agitator, thermometer and condenser. The mixture is heated under reflux for 1.5 hours, acidified with 5% HCl to pH 2 and heated under reflux for 3 hours. By cooling to 20° C. a precipitate is formed which is filtered off, washed with water and dried under vacuum. 4.7 g of 2,4-dioxo-3-azaspiro[5,5]undecane are obtained.

Example 7

Synthesis of 2,4-dioxo-3-azaspiro[5,5]undecane (VII)

204 ml of a 5.4 M solution of sodium methylate in methanol, 550 ml methanol and 145.5 g of dimethylmalonate are placed in a 2 litre flask equipped with a mechanical stirrer, thermometer and condenser, under nitrogen flow. After 30 minutes, 148 g of cyclohexylidenecyanoacetamide are added over a period of 30 minutes. The mixture is left under agitation for 1.5 hours at 30° C., after which 626 g of 15% NaOH are added, then heated under reflux for 1.5 hours. 400 ml of methanol are distilled and the mixture is acidified with 36% HCl to pH 3 then heated under reflux for 3 hours. By cooling to 25° C. a precipitate is formed which is filtered off, washed with water until the washing waters are neutral and dried under vacuum at 45° C. 69 g of 2,4-dioxo-3-azaspiro[5,5]undecane are obtained.

Example 8

Synthesis of cyclohexanediacetic acid monoamide (V)

9 g of 2,4-dioxo-3-azaspiro[5,5]undecane and 30 g of 10% NaOH are placed in a 250 ml flask equipped with mechanical agitator, thermometer and condenser. The mixture is heated under reflux for 1 hour, cooled to 25° C. and acidified with 36% HCl to pH 5. The precipitate formed is filtered off, washed with water and dried under vacuum. 6.4 g of cyclohexanediacetic acid monoamide are obtained.

The invention claimed is:
1. A compound of formula VI

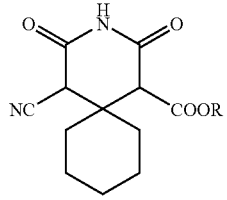

VI where R is chosen from hydrogen, alkyl, substituted alkyl, benzyl.

2. Process for preparing the compound of formula VI,

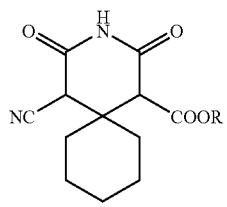

VI where R is chosen from hydrogen, alkyl, substituted alkyl, benzyl, comprising the following steps:

(i) condensing cyclohexanone with cyanoacetamide to obtain 2-cyclohexylidene-2-cyanoacetamide;
(ii) condensing said 2-cyclohexylidene-2-cyanoacetamide with a malonic acid ester of formula

where R' and R", the same or different, represent alkyd, substituted alkyl, benzyl.

3. Process as claimed in claim 2, wherein the malonic ester is chosen from ethyl malonate, methyl malonate, dibenzylmalonate.

4. Process as claimed in claim 2, wherein the passages (i) and (ii) are undertaken in a single reactor without isolating the intermediate compounds.

5. Process for preparing 3,3-pentamethylene glutaric monoamide, comprising by the following steps:

(a) subjecting the compound VI

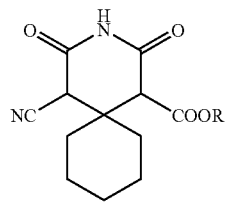

VI to hydrolysis and subsequent decarboxylation, where R is chosen from hydrogen, alkyl, substituted alkyl, benzyl, to obtain 2,4-dioxo-3-azaspiro[5,5]undecane;
(b) subjecting the 2,4-dioxo-3-azaspiro[5,5]undecane to further hydrolysis, to obtain 3,3-pentamethylene glutaric acid monoamide.

6. Process as claimed in claim 5, wherein the hydrolysis in step (a) takes place under basic conditions.

7. Process as claimed in claim 5, wherein the decarboxylation in step (a) takes place under acidic conditions.

8. Process as claimed in claim 5, wherein the hydrolysis in step (b) takes place under basic conditions.

9. Process as claimed in claim 5, achieved without isolating the intermediate compounds.

* * * * *